United States Patent
Dietrich et al.

(10) Patent No.: US 9,308,092 B2
(45) Date of Patent: Apr. 12, 2016

(54) DEVICE FOR ASSEMBLY OF BALL HEADS AND ADAPTER SLEEVES AS INTEGRATED COMPONENT PART OF THE PACKAGE

(75) Inventors: Martin Dietrich, Potenitz (DE); Patricie Merkert, Kirchheim u. Teck (DE); Roman Preuss, Leinf.-Echterdingen (DE); Paul Silberer, Waghausel (DE); Heinrich Wecker, Eckental (DE)

(73) Assignee: CeramTec GmbH, Plochingen (DE)

( * ) Notice: Subject to any disclaimer, the term of this patent is extended or adjusted under 35 U.S.C. 154(b) by 521 days.

(21) Appl. No.: 12/298,544
(22) PCT Filed: May 2, 2007
(86) PCT No.: PCT/EP2007/054246
§ 371 (c)(1), (2), (4) Date: Apr. 23, 2009
(87) PCT Pub. No.: WO2007/125125
PCT Pub. Date: Nov. 8, 2007

(65) Prior Publication Data
US 2009/0299484 A1    Dec. 3, 2009

(30) Foreign Application Priority Data

May 2, 2006 (DE) .......................... 10 2006 020 616
Jun. 20, 2006 (DE) .......................... 10 2006 028 720
Jun. 20, 2006 (DE) ...................... 20 2006 009 757 U

(51) Int. Cl.
| | |
|---|---|
| *A61F 2/36* | (2006.01) |
| *A61F 2/46* | (2006.01) |
| *A61F 2/34* | (2006.01) |
| *B65D 25/10* | (2006.01) |
| *A61F 2/00* | (2006.01) |

(Continued)

(52) U.S. Cl.
CPC ................. *A61F 2/34* (2013.01); *A61B 19/026* (2013.01); *A61F 2/0095* (2013.01);
(Continued)

(58) Field of Classification Search
CPC ... A61F 2/0095; A61F 2/3609; A61F 2/4637; A61F 2/30721; A61F 2002/30474; A61F 2002/30558; A61F 2002/4666; A61F 2220/0025; A61F 2250/0073; F16F 1/422; B65D 25/101
USPC .............. 206/438, 210, 205, 459.1, 363, 493, 206/303, 370, 591, 592; 623/22.4
See application file for complete search history.

(56) References Cited

U.S. PATENT DOCUMENTS 3,493,164 A * 2/1970 Edwards .................... 206/521.1
3,853,221 A * 12/1974 Boyd ............................ 206/592
(Continued)

FOREIGN PATENT DOCUMENTS

| EP | 0 133 393 A1 | 2/1985 |
|---|---|---|
| EP | 0 373 078 A1 | 6/1990 |

(Continued)

*Primary Examiner* — Andrew Perreault
(74) *Attorney, Agent, or Firm* — Norton Rose Fullbright US LLP

(57) ABSTRACT

The invention relates to a package for receiving an adapter sleeve for a hip endoprosthesis, the hip endoprosthesis comprising a ball head which has to be pushed onto the adapter sleeve with a defined pushing-on force. For simplification and secure fastening of the ball head on the adapter sleeve, it is proposed according to the invention that a device for the mounting of the ball head on the adapter sleeve is integrated in the package and this device comprises indicating elements which indicate that the defined pushing-on force has been reached when the ball head is pressed onto the adapter sleeve.

2 Claims, 3 Drawing Sheets

Figure 8:
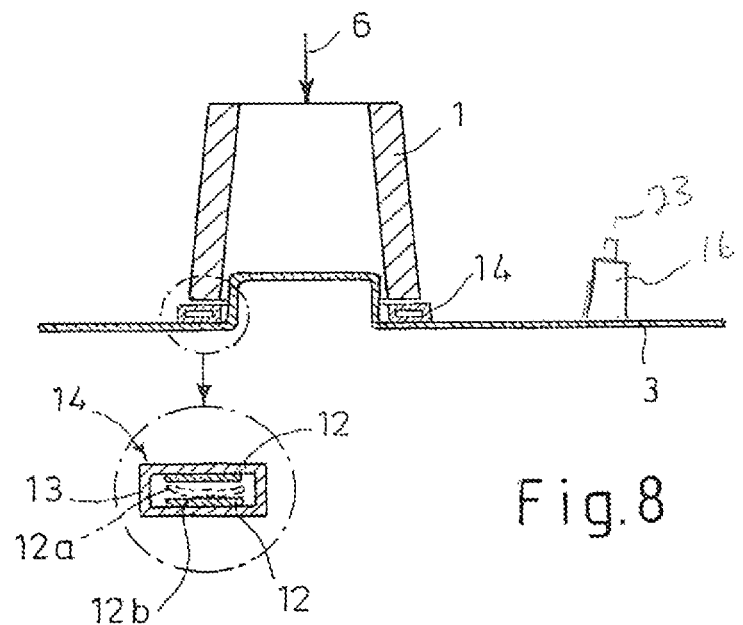

(51) Int. Cl.
 A61F 2/30 (2006.01)
 A61B 19/02 (2006.01)
 A61F 2/32 (2006.01)

(52) U.S. Cl.
 CPC .............. *A61F 2/30721* (2013.01); *A61F 2/32* (2013.01); *A61F 2/3609* (2013.01); *A61F 2/4637* (2013.01); *B65D 25/101* (2013.01); *A61B 2019/0267* (2013.01); *A61F 2002/30217* (2013.01); *A61F 2002/30332* (2013.01); *A61F 2002/30474* (2013.01); *A61F 2002/30558* (2013.01); *A61F 2002/365* (2013.01); *A61F 2002/3611* (2013.01); *A61F 2002/4666* (2013.01); *A61F 2002/4689* (2013.01); *A61F 2002/4697* (2013.01); *A61F 2220/0025* (2013.01); *A61F 2220/0033* (2013.01); *A61F 2230/0067* (2013.01); *A61F 2250/0073* (2013.01)

(56) References Cited

U.S. PATENT DOCUMENTS

| | | | |
|---|---|---|---|
| 4,542,825 A | | 9/1985 | Thomas et al. |
| 4,697,703 A | * | 10/1987 | Will .............................. 206/363 |
| 4,921,500 A | | 5/1990 | Averill |
| 5,133,765 A | | 7/1992 | Cuilleron |
| 5,193,679 A | | 3/1993 | White |
| 5,311,834 A | * | 5/1994 | Ross .............................. 116/306 |
| 5,336,268 A | | 8/1994 | Rispeter |
| 5,405,005 A | | 4/1995 | White |
| 5,685,427 A | * | 11/1997 | Kuitems et al. ................ 206/493 |
| 6,096,083 A | * | 8/2000 | Keller et al. ................ 623/22.11 |
| 6,206,929 B1 | * | 3/2001 | Ochoa et al. ................ 623/22.17 |
| 6,432,141 B1 | * | 8/2002 | Stocks et al. ................. 623/22.4 |
| 2004/0054373 A1 | | 3/2004 | Serra |
| 2004/0064145 A1 | | 4/2004 | Ball et al. |
| 2004/0225370 A1 | * | 11/2004 | Cruchet et al. ............. 623/22.18 |
| 2005/0246031 A1 | * | 11/2005 | Frederick et al. .......... 623/22.29 |
| 2006/0027027 A1 | | 2/2006 | Serra et al. |
| 2007/0034538 A1 | * | 2/2007 | Landis .......................... 206/363 |

FOREIGN PATENT DOCUMENTS

| | | |
|---|---|---|
| EP | 0 523 895 A1 | 1/1993 |
| EP | 0 547 354 A1 | 6/1993 |
| EP | 1 405 617 A2 | 4/2004 |
| FR | 2 656 792 A1 | 7/1991 |

\* cited by examiner

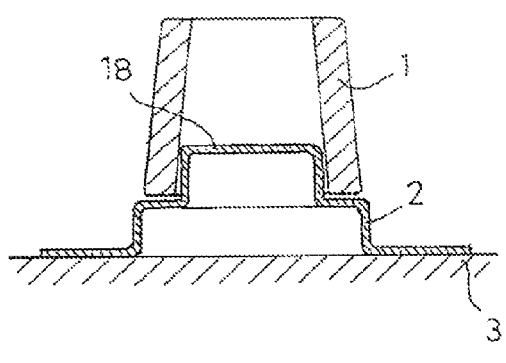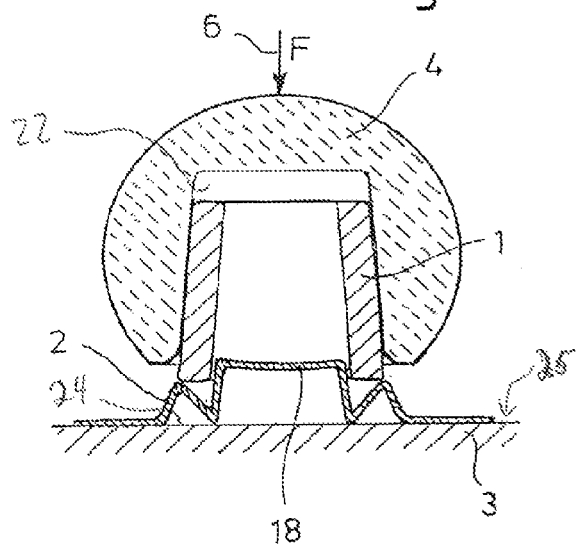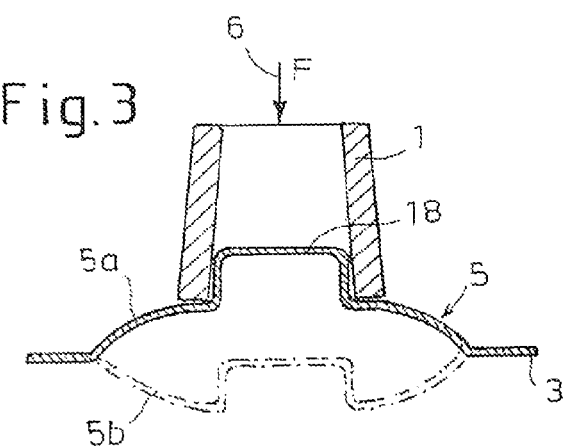

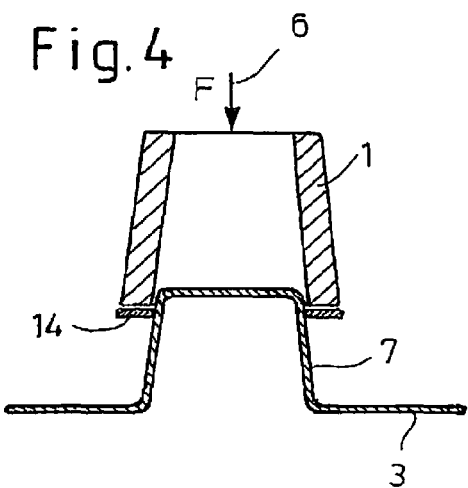
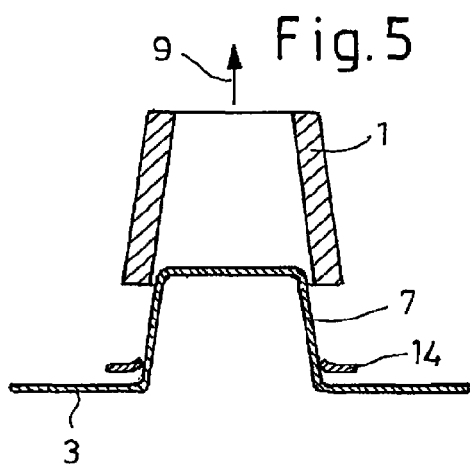
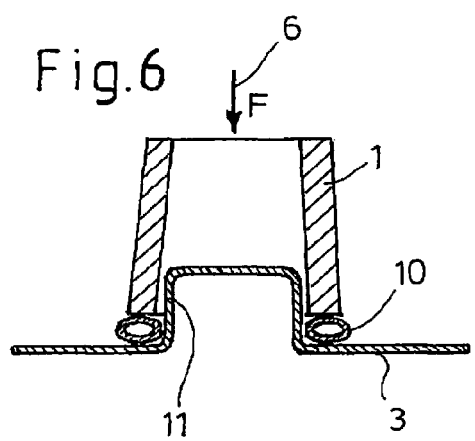
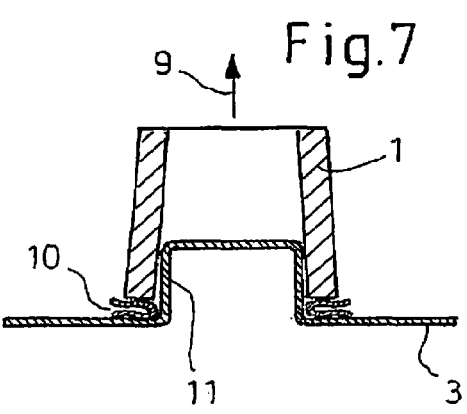

DEVICE FOR ASSEMBLY OF BALL HEADS AND ADAPTER SLEEVES AS INTEGRATED COMPONENT PART OF THE PACKAGE

This application is a §371 of PCT/EP2007/054246 filed May 2, 2007, which claims priority from DE 10 2006 020 616.9 filed May 2, 2006, DE 20 2006 009 757.0 filed Jun. 20, 2006 and DE 10 2006 028 720.7 filed Jun. 20, 2006.

The invention relates to a package for receiving an adapter sleeve for a hip endoprosthesis, the hip endoprosthesis comprising a ball head which has to be pushed onto the adapter sleeve with a defined pushing-on force.

On the market there are various modular systems for hip endoprostheses in which the ball head is seated on an adapter sleeve and the latter in turn is seated on the prosthesis cone. The components in these systems are generally ones which are connected to one another via conical clamping connections. Furthermore, all the parts are generally delivered separately and not preassembled, in order to avoid changes of the plug connections owing to external influences during transportation.

Three problems arise here.

1. It must be clear to the user performing the assembly of the components in what order the assembly is to be carried out.

2. It must be clear to the user, particularly in the case of conical plug connections, with what initial force the components are to be joined.

3. The plug connection of the ball head and adapter sleeve must be clean. There must be no dirt particles present on the contact surface.

The present invention offers a solution to all three problems:

According to the invention, a device for the mounting of the ball head on the adapter sleeve is integrated in the package and this device comprises indicating elements which indicate that the defined pushing-on force has been reached when the ball head is pressed onto the adapter sleeve. As a result, the assembly is simplified and the user can tell whether he has pushed the ball head onto the adapter sleeve with the necessary pushing-on force.

In one embodiment according to the invention, the device for the mounting comprises a projection of the package, which projection can be pressed in as far as a stop and on which the adapter sleeve is placed, and the stop indicates that the necessary pushing-on force has been reached when the ball head is pressed onto the adapter sleeve.

The material and/or the configuration of the projection which can be pressed in is chosen so that the projection touches the stop only when the necessary pushing-on force has been reached. The stop may also be the bottom of the package.

Preferably, the projection is designed so that it can buckle in the region of the front end of the adapter sleeve.

In another embodiment, the device for the mounting of the ball head on the adapter sleeve is designed as a yielding, collapsible structure and the collapsing of the structure indicates that the necessary pushing-on force has been reached when the ball head is pressed onto the adapter sleeve.

Preferably, the structure is designed so that it produces a sound, such as, for example, a click, when it collapses.

In an advantageous configuration, a package anti-abrasion disc is arranged between the adapter sleeve and the projection or the package, so that the adapter sleeve does not touch the projection and/or the package. As a result, no abrasion of material from the package occurs, which could be deposited on the adapter sleeve or the ball head and lead to problems during the implantation.

In one embodiment according to the invention, the package anti-abrasion disc is designed as an air cushion which bursts when the force with which the ball head is being pushed onto the adapter sleeve is large enough. The bursting indicates to the user that the pushing-on force is large enough.

In another embodiment of the invention, the package anti-abrasion disc is designed as a spatial structure deformable through the effect of force, the structure comprising means which are spaced from one another and touch only when the force with which the ball head is being pushed onto the adapter sleeve is large enough.

Advantageously, the means are laminas which are separated from one another by a spacer.

In one embodiment of the invention, a chemical reaction with a change of colour is triggered by the materials or coating of the means or the laminas when they touch. As a result, the user can tell when the pushing-on force is large enough.

In an alternative embodiment according to the invention, a piezoelectric element which measures and indicates the pushing-on force or initiates the indication is arranged between the adapter sleeve and the package, optionally in addition, to the package anti-abrasion disc, it being possible for the indicating element 23 to be, for example, a lamp or a sound generator.

In another embodiment of the invention, the projection is designed as a conical peg on which a package anti-abrasion disc is arranged in a manner displaceable in the longitudinal direction of the peg on pressure application, and the adapter sleeve when encompassing the peg sits on the package anti-abrasion disc and displaces the package anti-abrasion disc when the ball head is pressed onto the adapter sleeve.

Advantageously, the point up to which the package anti-abrasion disc has to be displaced when pressure is being applied to the adapter sleeve by the ball head is marked or is a stop, such as, for example, the bottom of the package.

Advantageously, a ball head is also removably positioned in the package at the same time, and the ball head can be removed separately.

The invention is thus distinguished by the fact that the ball head and the adapter sleeve are positioned in a package such that the ball head can be removed separately. The adapter sleeve remains in the package and the ball head is then pushed directly onto the adapter sleeve still situated in the package. Furthermore, there is integrated in the package a device which delivers feedback to the user when the necessary pushing-on force has been reached when the ball head is pressed onto the adapter sleeve. The feedback here may, for example, be tactile or by visual or audio signals.

The invention is explained in more detail below with the aid of various figures.

FIG. 1 shows in cross-section an adapter sleeve 1, which is seated in a raised manner on a cylindrical projection 2 of a device 20 for mounting of ball head 4 on adapter sleeve 1 is integrated in package 3. This is the state in which the package 3 is delivered, What is not shown is that, in addition to the adapter sleeve 1, a ball head is also removably arranged in the package 3 in any way. In order that the adapter sleeve 1 does not move on the projection 2, a cylinder 18, the diameter of which corresponds to the inside diameter of the adapter sleeve 1 at the front end, is arranged on the projection 2.

FIG. 2 shows the package 3 according to FIG. 1 shortly after use. The ball head 4 having a cavity 22 for receiving adapter sleeve 1 therein has been placed on the adapter sleeve 1. With increasing pressure of the ball head 4 on the adapter sleeve 1, the cylindrical projection 2 gives way until the base 25 of the package 3 is reached. The base acts as a mechanical stop 24 so to speak and signals that a sufficient force has been applied (tactile feedback). The material or the configuration of the cylindrical projection 2 must be chosen so that the latter touches the base of the package 3 only when the ball head 4 is pressed onto the adapter sleeve 1 with sufficient pressure.

FIG. 3 shows an embodiment in which the projection of the package 3 is designed as a yielding, collapsible structure 5, so that when the necessary force is reached the structure 5 collapses and a click can be heard (tactile and audio feedback). The reference symbol 5a denotes the structure in the non-collapsed state, i.e. in the starting state. The broken line 5b shows the structure in the collapsed state, i.e. that the force applied has been sufficient.

The force applied by the ball head is indicated in this figure and also the following figures by the arrow 6.

FIG. 4 shows a projection of the package 3 which is designed as a conical peg 7, with the adapter sleeve 1 being pushed onto this peg 7. Located under the adapter sleeve 1 on the peg 7 of the projection is a package anti-abrasion disc 14, which is intended to prevent the adapter sleeve 1 and the package 3 from touching. As a result, no abrasion of material from the package 3 occurs, which could be deposited on the adapter sleeve 1 or the ball head and lead to problems during the implantation.

When the package anti-abrasion disc 14 remains displaced in a defined manner on the conical peg 7 after the ball head has been pressed onto the adapter sleeve 1, then the pushing-on force has been sufficient. The point up to which the package anti-abrasion disc 14 has to be displaced for the pushing-on force to be sufficient is advantageously marked or is the bottom of the package 3.

FIG. 5 shows the package according to FIG. 4 in the displaced state of the package anti-abrasion disc 14. The arrow 9 indicates the lifting-off of the ball head, which is now firmly connected to the adapter sleeve 1, from the peg 7. The ball head is not shown here.

FIG. 6 shows an embodiment in which the package anti-abrasion disc is designed as an air cushion 10 which bursts when the ball head is pressed with sufficient force onto the adapter sleeve 1. This is shown in FIG. 7. The projection 11 is preferably of cylindrical form in this embodiment and corresponds to the cylinder 18 of FIG. 1.

FIG. 8 shows a package anti-abrasion disc 14 which is composed of two laminas 12 separated by a spacer 13. When sufficient pressure is exerted on the adapter sleeve 1 by the ball head, at least one of the laminas 12 in the package anti-abrasion disc 14 is deformed to such a degree that it touches the other lamina 12. This could be indicated in various ways. Preferably, a chemical reaction with a change of colour could be triggered by the materials or coatings of the laminas 12. The broken line 12a denotes the lamina which has been bent through the effect of force and is touching the other lamina 12b.

Figure 9:
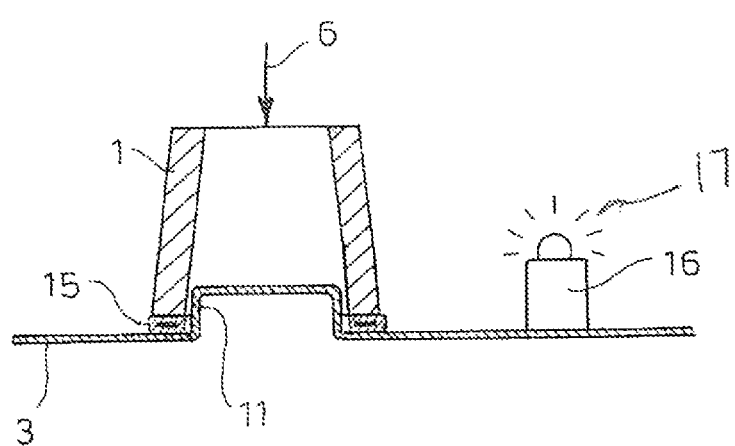

FIG. 9 shows an embodiment in which a sufficient pressure of the ball head on the adapter sleeve 1 or on the package anti-abrasion disc is measured and indicated electronically/electrically, for example, by piezoelectric elements 15 and feedback to a signal generator 16. The signal generator 16 could, for example, be a lamp or a sound generator.

The invention claimed is:

1. A kit comprising
    a ball head for a hip prosthesis, the ball head having a cavity with an inner diameter therein;
    a package comprising a base, the package further comprising a cylindrical projection thereon;
    an adapter sleeve arranged on the cylindrical projection, receives the cavity of the ball head for a hip prosthesis, the adapter sleeve having a hollow end with an inside diameter;
    wherein the cylindrical projection has a cylinder having a diameter which corresponds to the inside diameter of the adapter sleeve;
    and where the base acts as a mechanical stop and signals that a sufficient force has been applied when the cylinder is forced to the base when the ball head is pressed onto the adapter sleeve with a sufficient force.

2. The kit according to claim 1, wherein the projection is designed to buckle in a region of a front end of the adapter sleeve.

* * * * *